(12) United States Patent
Kim et al.

(10) Patent No.: US 10,320,032 B2
(45) Date of Patent: Jun. 11, 2019

(54) ORGANIC ELECTROLYTIC SOLUTION AND LITHIUM BATTERY USING THE SAME

(71) Applicant: SAMSUNG SDI CO., LTD., Yongin-si, Gyeonggi-do (KR)

(72) Inventors: AeRan Kim, Yongin-si (KR); MiYoung Son, Yongin-si (KR); HyunBong Choi, Yongin-si (KR); MyungHeui Woo, Yongin-si (KR); SeungTae Lee, Yongin-si (KR); HaRim Lee, Yongin-si (KR); AeHui Goh, Yongin-si (KR); WooCheol Shin, Yongin-si (KR)

(73) Assignee: Samsung SDI Co., Ltd., Yongin-Si, Gyeonggi-do (KR)

( * ) Notice: Subject to any disclaimer, the term of this patent is extended or adjusted under 35 U.S.C. 154(b) by 115 days.

(21) Appl. No.: 15/459,672

(22) Filed: Mar. 15, 2017

(65) Prior Publication Data
US 2017/0271715 A1 Sep. 21, 2017

(30) Foreign Application Priority Data
Mar. 18, 2016 (KR) ........................ 10-2016-0032732

(51) Int. Cl.
*H01M 10/0567* (2010.01)
*C07D 333/48* (2006.01)
(Continued)

(52) U.S. Cl.
CPC ...... *H01M 10/0567* (2013.01); *C07D 327/04* (2013.01); *C07D 333/48* (2013.01);
(Continued)

(58) Field of Classification Search
CPC .......... H01M 10/0567; H01M 10/052; H01M 10/0568; H01M 2300/0025;
(Continued)

(56) References Cited

U.S. PATENT DOCUMENTS

| | | | |
|---|---|---|---|
| 2,494,515 A | 1/1950 | Morris et al. | |
| 3,907,597 A * | 9/1975 | Mellors ................... | H01M 6/16 429/327 |

(Continued)

FOREIGN PATENT DOCUMENTS

| | | |
|---|---|---|
| EP | 2 778 158 A1 | 9/2014 |
| KR | 10-2013-0054214 A | 5/2013 |

*Primary Examiner* — Amanda C. Walke
(74) *Attorney, Agent, or Firm* — Lee & Morse, P.C.

(57) ABSTRACT

Provided is an organic electrolyte solution that includes a lithium salt, an organic solvent, and a sulfonate ester-based compound represented by Formula 1:

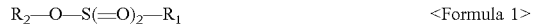

$$R_2\text{—}O\text{—}S(\text{=}O)_2\text{—}R_1 \qquad <\text{Formula 1}>$$

wherein, in Formula 1, $R_1$ may be a C1-C20 alkyl group that is unsubstituted or substituted with halogen, a C5-C20 cycloalkyl group that is unsubstituted or substituted with halogen, a C6-C40 aryl group that is unsubstituted or substituted with halogen, or a C2-C40 heteroaryl group that is unsubstituted or substituted with halogen, and $R_2$ may be a substituted or unsubstituted cyclic sulfone group.

15 Claims, 2 Drawing Sheets

(51) Int. Cl.
  *C07D 327/04*   (2006.01)
  *H01M 10/052*   (2010.01)
  *H01M 10/0568*  (2010.01)

(52) U.S. Cl.
  CPC ..... *H01M 10/052* (2013.01); *H01M 10/0568* (2013.01); *H01M 2300/0025* (2013.01); *H01M 2300/0037* (2013.01)

(58) Field of Classification Search
  CPC ......... H01M 2300/0037; C07C 317/02; C07C 317/04; C07C 317/06; C07C 317/12
  USPC ........................................................ 429/199
  See application file for complete search history.

(56) References Cited

U.S. PATENT DOCUMENTS

| | | | |
|---|---|---|---|
| 4,029,587 A | 6/1977 | Koch | |
| 4,029,588 A | 6/1977 | Koch | |
| 4,167,458 A * | 9/1979 | Louzos | C25D 3/54 205/234 |
| 9,318,776 B2 * | 4/2016 | Abe | H01M 10/0525 |
| 9,583,272 B2 * | 2/2017 | Oyama | H01G 9/035 |
| 9,608,287 B2 * | 3/2017 | Abe | C07D 327/04 |
| 9,966,632 B2 * | 5/2018 | Abe | H01M 10/0567 |
| 2009/0280414 A1 * | 11/2009 | Koh | H01M 4/13 429/304 |
| 2012/0034532 A1 * | 2/2012 | Kim | H01M 10/052 429/331 |
| 2013/0280600 A1 * | 10/2013 | Uehara | H01M 4/505 429/200 |
| 2014/0242472 A1 * | 8/2014 | An | H01M 10/0567 429/332 |
| 2014/0319423 A1 | 10/2014 | Cooper | |
| 2015/0284326 A1 * | 10/2015 | Priem | C07D 327/04 530/327 |
| 2015/0287984 A1 * | 10/2015 | Kong | H01M 4/1315 429/223 |
| 2017/0025321 A1 * | 1/2017 | Homma | H01L 23/3142 |
| 2017/0098859 A1 * | 4/2017 | Murakami | H01M 10/0569 |
| 2018/0248226 A1 * | 8/2018 | Kono | H01M 10/0567 |

* cited by examiner

ORGANIC ELECTROLYTIC SOLUTION AND LITHIUM BATTERY USING THE SAME

CROSS-REFERENCE TO RELATED APPLICATION

Korean Patent Application No. 10-2016-0032732, filed on Mar. 18, 2016, in the Korean Intellectual Property Office, and entitled: "Organic Electrolytic Solution and Lithium Battery Using the Same," is incorporated by reference herein in its entirety.

BACKGROUND

1. Field

One or more embodiments relate to an organic electrolyte solution and a lithium battery using the electrolyte solution.

2. Description of the Related Art

Lithium batteries are used as driving sources of portable electronic devices sources, such as camcorders, mobile phones, and laptop computers. Lithium secondary batteries are rechargeable at high rates and have a high energy density per unit weight of about three times higher than that of lead storage batteries, nickel-cadmium (Ni—Cd) batteries, nickel-hydrogen batteries, and nickel-zinc batteries.

SUMMARY

Embodiments are directed to an organic electrolyte solution that includes a lithium salt, an organic solvent, and a sulfonate ester-based compound represented by Formula 1,

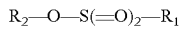  <Formula 1> wherein, in Formula 1, $R_1$ is a C1-C20 alkyl group that is unsubstituted or substituted with halogen, a C5-C20 cycloalkyl group that is unsubstituted or substituted with halogen, a C6-C40 aryl group that is unsubstituted or substituted with halogen, or a C2-C40 heteroaryl group that is unsubstituted or substituted with halogen, and $R_2$ is a substituted or unsubstituted cyclic sulfone group.

Embodiments are also directed to a lithium battery that includes a cathode, an anode, and the organic electrolyte solution.

BRIEF DESCRIPTION OF THE DRAWINGS

Features will become apparent to those of skill in the art by describing in detail example embodiments with reference to the attached drawings in which.

DETAILED DESCRIPTION

Figure 1:
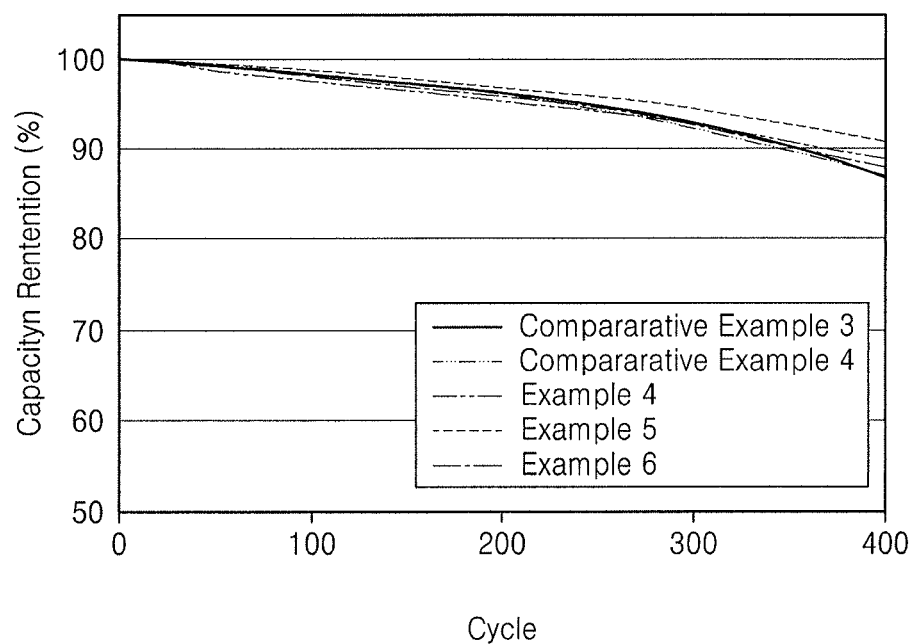
FIG. 1 illustrates a graph that shows room temperature lifespan characteristics of lithium batteries prepared in Example 4 and Comparative Example 3.

Example embodiments will now be described more fully hereinafter with reference to the accompanying drawings, however, they may be embodied in different forms and should not be construed as limited to the embodiments set forth herein. Rather, these embodiments are provided so that this disclosure will be thorough and complete, and will fully convey example implementations to those skilled in the art.

In the drawing figures, the dimensions of layers and regions may be exaggerated for clarity of illustration. Like reference numerals refer to like elements throughout.

As used herein, the term "and/or" includes any and all combinations of one or more of the associated listed items. Expressions such as "at least one of," when preceding a list of elements, modify the entire list of elements and do not modify the individual elements of the list.

Hereinafter, according to example embodiments, an organic electrolyte solution and a lithium battery using the electrolyte solution will be described.

According to an embodiment, an organic electrolyte solution includes a first lithium salt, an organic solvent, and a sulfonate ester-based compound represented by Formula 1:

  <Formula 1>

In Formula 1, R1 may be a C1-C20 alkyl group that is unsubstituted or substituted with halogen, a C5-C20 cycloalkyl group that is unsubstituted or substituted with halogen, a C6-C40 aryl group that is unsubstituted or substituted with halogen, or substituted or unsubstituted with halogen a C2-C40 heteroaryl group, and $R_2$ may be a substituted or unsubstituted cyclic sulfone group.

As an additive, the organic electrolyte solution for lithium battery including the sulfonate ester-based compound may improve battery performance such as high-temperature characteristics or lifespan characteristics of a lithium battery.

The sulfonate ester-based compound has a structure in which a cyclic sulfone group linked to a sulfonate group.

Without being bound by theory, it is believed that the cyclic sulfone group included in the sulfonate ester-based compound may accept electrons from an anode surface during a charging process and reduce itself, or react with a reduced polar solvent molecule, and may influence a property of a solid electrolyte interface (SEI) layer. For example, the sulfonate ester-based compound including the cyclic sulfone group may easily accept electrons from an anode compared to the polar solvent. Thus, the sulfonate ester-based compound may be reduced at a voltage lower than that at which the polar solvent reduces, and thus the sulfonate ester-based compound may be reduced before the polar solvent reduces.

For example, the sulfonate ester-based compound may be more easily reduced and/or decomposed into radicals and/or ions during a charging process by including the cyclic sulfone group. Thus, when the resulting radicals and/or ions bind to lithium ions to form an SEI layer suitable for an anode, a formation of additional decomposition products derived from the solvents may be suppressed. For example, the sulfonate ester-based compound may form a covalent bond with various functional groups on a carbonaceous anode surface or a carbonaceous anode, or may be adsorbed on an electrode surface. Through this binding and/or adsorption, a modified SEI layer with improved stability capable of maintaining a durable state after a long period of charging/discharging process (compared to an SEI layer that is only formed by using an organic solvent) may be formed. Also, such a durable, modified SEI layer may help prevent the organic solvent, in which lithium ions are solvated, from entering into the electrode during intercalation of the lithium ions. Thus, the modified SEI layer may block direct contact between the organic solvent and the anode, such that reversibility of intercalation/deintercalation of lithium ions further improves, which may result in increasing a discharge capacity and improving lifespan characteristics of the battery.

Also, the sulfonate ester-based compound may be coordinated on a cathode surface by including the cyclic sulfone group and thus may influence a property of a protection layer that is formed on the cathode surface. For example, the cyclic sulfone group may be coordinated with a transition metal ion of a cathode active material and thus may form a complex. Through a formation of the complex, a modified protection layer with improved stability capable of maintaining a durable state after a long period of charging/discharging process compared to a protection that is only formed by using an organic solvent can be formed. Also, such durable, modified protection layer may effectively prevent the organic solvent, in which lithium ions are solvated, from entering into the electrode during intercalation of the lithium ions. Therefore, the modified protection layer may block direct contact between the organic solvent and the cathode, such that reversibility of intercalation/deintercalation of lithium ions further improves, which may result in increasing stability and improving lifespan characteristics of the battery.

Also, the sulfonate ester-based compound may have a substituent which is bound to a cyclic sulfone ring via —O—S(=O)$_2$-bond, compared to a general cyclic sulfone-based compound, wherein the substituents are directly bound to the cyclic sulfone ring, and thus may have a relatively high molecular weight, which may result in thermal stability.

The sulfonate ester-based compound may form an SEI layer on an anode surface or a protection layer on a cathode surface. The sulfonate ester-based compound may be thermally stable, and high-temperature stability and lifespan characteristics of a lithium battery may improve.

In an example embodiment, in Formula 1, $R_2$ may be a cyclic sulfone group represented by Formula 2:

<Formula 2>

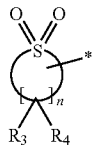

In Formula 2, $R_3$ and $R_4$ may each independently be hydrogen, a C1-C20 alkyl group that is unsubstituted or substituted with halogen, a C2-C20 alkenyl group that is unsubstituted or substituted with halogen, a C2-C20 alkynyl group that is unsubstituted or substituted with halogen, a C5-C20 cycloalkyl group that is unsubstituted or substituted with halogen, a C6-C40 aryl group that is unsubstituted or substituted with halogen, a C2-C40 heteroaryl group that is unsubstituted or substituted with halogen, or a polar functional group including at least one heteroatom, n may be an integer selected from 4 to 9, and * represents the $R_2$-oxygen bond in Formula 2.

For example, the polar functional group including at least one heteroatom may include at least one selected from —F, —Cl, —Br, —I, —C(=O)OR$^{16}$, —OR$^{16}$, —OC(=O)OR$^{16}$, —R$^{15}$OC(=O)OR$^{16}$, —C(=O)R$^{16}$, —R$^{15}$C(=O)R$^{16}$, —OC(=O)R$^{16}$, —R$^{15}$OC(=O)R$^{16}$, —C(=O)—O—C(=O)R$^{16}$, —R$^{15}$C(=O)—O—C(=O)R$^6$, —SR$^{16}$, —R$^{15}$SR$^{16}$, —SSR$^{16}$, —R$^{15}$SSR$^{16}$, —S(=O)R$^{16}$, —R$^{15}$S(=O)R$^{16}$, —R$^{12}$C(=S)R$^{16}$, —R$^{15}$C(=S)SR$^{16}$, —R$^{15}$SO$_3$R$^{16}$, —SO$_3$R$^{16}$, —NNC(=S)R$^{16}$, —R$^{15}$NNC(=S)R$^{16}$, —R$^{15}$N=C=S, —NCO, —R$^{15}$—NCO, —NO$_2$, —R$^{15}$NO$_2$, —R$^{15}$SO$_2$R$^{16}$, —SO$_2$R$^{16}$,

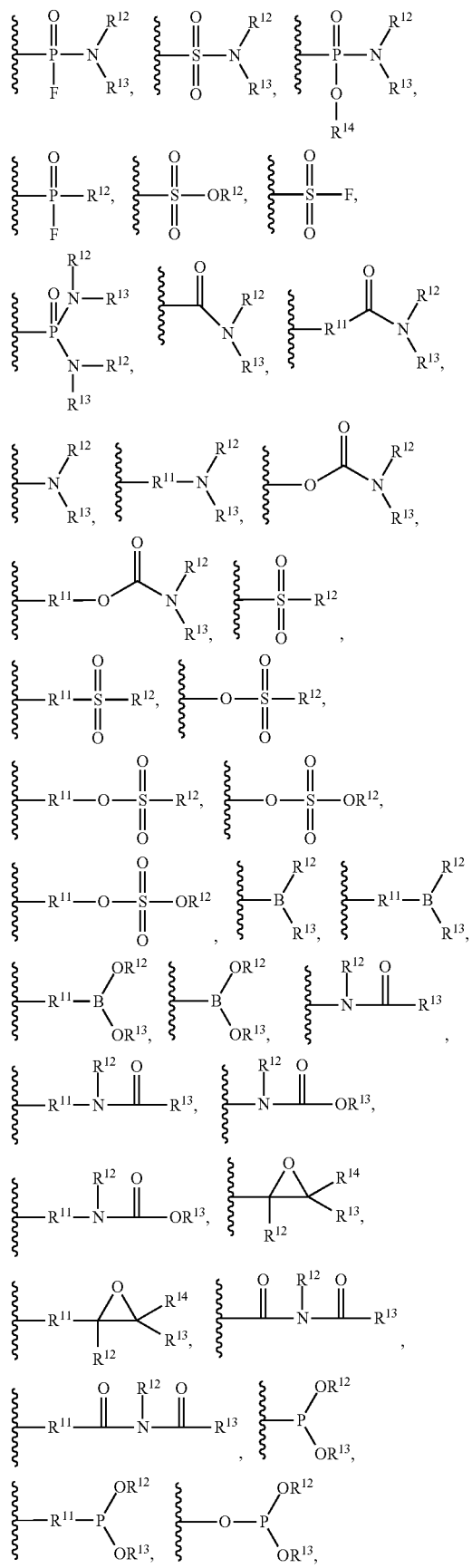

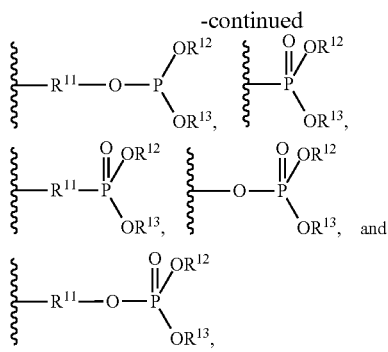

wherein $R^{11}$ and $R^{15}$ may each independently be a C1-C20 alkylene group that is unsubstituted or substituted with halogen, a C2-C20 alkenylene group that is unsubstituted or substituted with halogen, a C2-C20 alkynylene group that is unsubstituted or substituted with halogen, a C3-C12 cycloalkylene group that is unsubstituted or substituted with halogen, a C6-C40 arylene group that is unsubstituted or substituted with halogen, a C2-C40 heteroarylene group that is unsubstituted or substituted with halogen, a C7-C15 alkylarylene group that is unsubstituted or substituted with halogen, or a C7-C15 aralkylene group that is unsubstituted or substituted with halogen, and $R^{12}$, $R^{13}$, $R^{14}$ and $R^{16}$ may each independently be hydrogen, a halogen, a C1-C20 alkyl group that is unsubstituted or substituted with halogen, a C2-C20 alkenyl group that is unsubstituted or substituted with halogen, a C2-C20 alkynyl group that is unsubstituted or substituted with halogen, a C3-C12 cycloalkyl group that is unsubstituted or substituted with halogen, a C6-C40 aryl group that is unsubstituted or substituted with halogen, a C2-C40 heteroaryl group that is unsubstituted or substituted with halogen, a C7-C15 alkylaryl group that is unsubstituted or substituted with halogen, a C7-C15 trialkylsilyl group that is unsubstituted or substituted with halogen, or a C7-C15 aralkyl group that is unsubstituted or substituted with halogen.

For example, the halogen substituted to an alkyl group, an alkenyl group, an alkynyl group, a cycloalkyl group, an aryl group, a heteroaryl group, an alkylaryl group, a trialkylsilyl group, or an aralkyl group included in the polar functional group including a heteroatom may be fluorine (F).

For example, in Formula 1, $R_2$ may be a substituted or unsubstituted sulfolanyl group. When $R_2$ is a sulfolanyl group, high-temperature stability and lifespan characteristics of a lithium battery may improve.

For example, the substituent of the sulfolanyl group may be a C1-C20 alkyl group that is unsubstituted or substituted with halogen, a C2-C20 alkenyl group that is unsubstituted or substituted with halogen, a C2-C20 alkynyl group that is unsubstituted or substituted with halogen, a C5-C20 cycloalkyl group that is unsubstituted or substituted with halogen, a C6-C40 aryl group that is unsubstituted or substituted with halogen, a C2-C40 heteroaryl group that is unsubstituted or substituted with halogen, or a polar functional group including at least one heteroatom.

For example, in the organic electrolyte solution, the sulfonate ester-based compound of Formula 1 may be represented by Formula 3 or Formula 4:

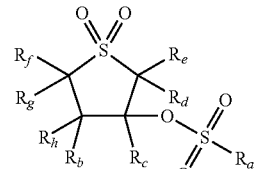
<Formula 3>

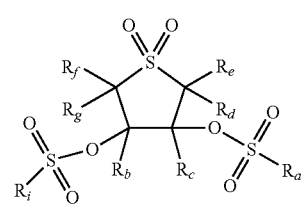
<Formula 4>

In Formula 3 and Formula 4, $R_a$ and $R_i$ may each independently be a halogen, a C1-C20 alkyl group that is unsubstituted or substituted with halogen, a C5-C20 cycloalkyl group that is unsubstituted or substituted with halogen, a C6-C40 aryl group that is unsubstituted or substituted with halogen, or a C2-C40 heteroaryl group that is unsubstituted or substituted with halogen, and $R_b$, $R_c$, $R_d$, $R_e$, $R_f$, $R_g$, and $R_h$ may each independently be hydrogen, a halogen, a C1-C20 alkyl group that is unsubstituted or substituted with halogen, a C2-C20 alkenyl group that is unsubstituted or substituted with halogen, a C2-C20 alkynyl group that is unsubstituted or substituted with halogen, a C1-C20 alkoxy group that is unsubstituted or substituted with halogen, a C5-C20 cycloalkyl group that is unsubstituted or substituted with halogen, a C6-C40 aryl group that is unsubstituted or substituted with halogen, or a C2-C40 heteroaryl group that is unsubstituted or substituted with halogen.

For example, $R_a$ and $R_i$ may each independently be a halogen, or a C1-C20 alkyl group that is unsubstituted or substituted with halogen. For example, $R_a$ and $R_i$ may each independently be a perfluoroalkyl group, which is an alkyl group that has all hydrogens replaced with fluorine.

For example, $R_a$ and $R_i$ may each independently be F, Cl, Br, I, a methyl group, an ethyl group, a propyl group, an isopropyl group, a butyl group, a tert-butyl group, a trifluoromethyl group, a tetrafluoroethyl group, a phenyl group, a naphthyl group, a tetrafluorophenyl group, a pyrrolyl group, or a pyridinyl group, and $R_b$, $R_c$, $R_d$, $R_e$, $R_f$, $R_g$, and $R_h$ may each independently be hydrogen, F, Cl, Br, I, a methyl group, an ethyl group, a propyl group, an isopropyl group, a butyl group, a tert-butyl group, a trifluoromethyl group, a tetrafluoroethyl group, a phenyl group, a naphthyl group, a tetrafluorophenyl group, a pyrrolyl group, or a pyridinyl group.

For example, in the organic electrolyte solution, the sulfonate ester-based compound represented by Formula 1 may be represented by Formula 5 or Formula 6:

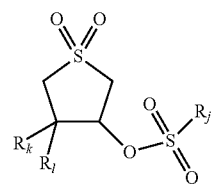
<Formula 5>

<Formula 6>

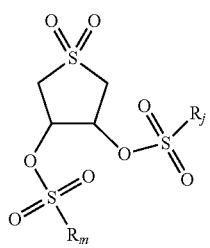

In Formula 5 and Formula 6, $R_j$ and $R_m$ may each independently be a halogen, a C1-C20 alkyl group that is unsubstituted or substituted with halogen, a C6-C40 aryl group that is unsubstituted or substituted with halogen, or a C2-C40 heteroaryl group that is unsubstituted or substituted with halogen, and $R_k$ and $R_l$ may each independently be hydrogen, a halogen, a C1-C20 alkyl group that is unsubstituted or substituted with halogen, a C6-C40 aryl group that is unsubstituted or substituted with halogen, or a C2-C40 heteroaryl group that is unsubstituted or substituted with halogen.

For example, $R_j$ and $R_m$, may each independently be a halogen, or a C1-C20 alkyl group that is unsubstituted or substituted with halogen. For example, $R_j$ and $R_m$, may each independently be a perfluoroalkyl group, which is an alkyl group that has all hydrogen substituted with fluorine.

For example, $R_j$ and $R_m$ may each independently be F, Cl, Br, I, a methyl group, an ethyl group, a propyl group, an isopropyl group, a butyl group, a tert-butyl group, a trifluoromethyl group, a tetrafluoroethyl group, a phenyl group, a naphthyl group, a tetrafluorophenyl group, a pyrrolyl group, or a pyridinyl group, and $R_k$ and $R_l$ may each independently be F, Cl, Br, I, a methyl group, an ethyl group, a propyl group, an isopropyl group, a butyl group, a tert-butyl group, a trifluoromethyl group, a tetrafluoroethyl group, a phenyl group, a naphthyl group, a tetrafluorophenyl group, a pyrrolyl group, or a pyridinyl group.

For example, in the organic electrolyte solution, the sulfonate ester-based compound represented by Formula 1 may be represented by one of Formulae 7 to 22:

<Formula 7>

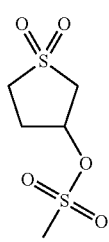

<Formula 8>

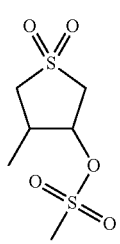

<Formula 9>

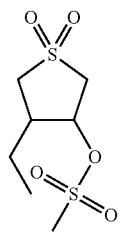

<Formula 10>

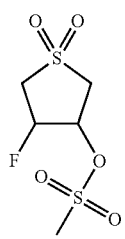

<Formula 11>

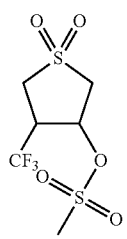

<Formula 12>

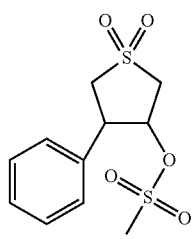

<Formula 13>

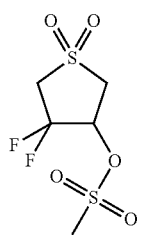

<Formula 14>

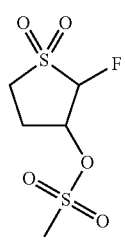

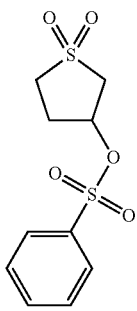
<Formula 15>

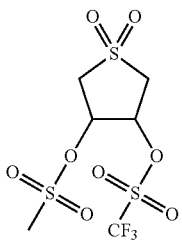
<Formula 21>

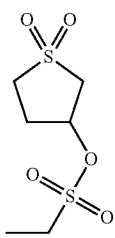
<Formula 16>

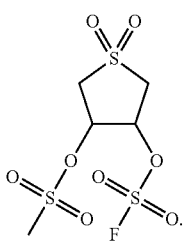
<Formula 22>

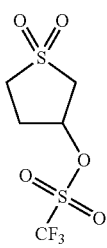
<Formula 17>

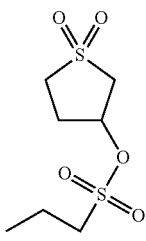
<Formula 18>

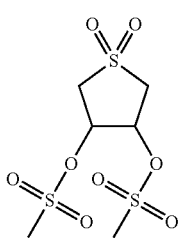
<Formula 19>

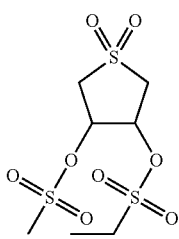
<Formula 20>

As used herein, 'a' and 'b' in the term "Ca-Cb" denote the number of carbons in a particular functional group. Thus, the functional group may include 'a' to 'b' carbon atoms. For example, "a C1-C4 alkyl group" denotes an alkyl group having 1 to 4 carbon atoms, and examples of the C1-C4 alkyl group may include $CH_3-$, $CH_3CH_2-$, $CH_3CH_2CH_2-$, $(CH_3)_2CH-$, $CH_3CH_2CH_2CH_2-$, $CH_3CH_2CH(CH_3)-$, and $(CH_3)_3C-$.

As used herein, a particular radical may refer to a monoradical or a di-radical depending on the context. For example, when a substituent needs two binding sites for binding with the rest of the molecule, the substituent may be understood as a di-radical. For example, a substituent specified as an alkyl group that needs two binding sites may be a di-radical, such as $-CH_2-$, $-CH_2CH_2-$, or $-CH_2CH(CH_3)CH_2-$. The term "alkylene" indicates that the radical means a di-radical.

As used herein, the terms "alkyl group" or "alkylene group" refers to a branched or non-branched aliphatic hydrocarbon group. For example, the alkyl group may be substituted or not. Non-limiting examples of the alkyl group are a methyl group, an ethyl group, a propyl group, an isopropyl group, a butyl group, an isobutyl group, a tert-butyl group, a pentyl group, a hexyl group, a cyclopropyl group, a cyclopentyl group, a cyclohexyl group, and a cycloheptyl group, each of which may be optionally substituted or not. In some embodiments, the alkyl group may have 1 to 6 carbon atoms. For example, a C1-C6 alkyl group may be a methyl group, an ethyl group, a propyl group, an isopropyl group, a butyl group, an isobutyl group, a sec-butyl group, a 1-pentyl group, a 3-pentyl group, or a hexyl group, but is not limited thereto.

As used herein, the term "cycloalkyl group" refers to a carbocyclic ring or ring system that is fully saturated. For example, the "cycloalkyl group" may refer to a cyclopropyl group, a cyclobutyl group, a cyclopentyl group, or a cyclohexyl group.

As used herein, the term "alkenyl group" refers to a hydrocarbon group including 2 to 20 carbon atoms with at least one carbon-carbon double bond. Non-limiting examples of the alkenyl group are an ethenyl group, a 1-propenyl group, a 2-propenyl group, a 2-methyl-1-propenyl group, a 1-butenyl group, a 2-butenyl group, a cyclopropenyl group, a cyclopentenyl group, a cyclohexcenyl group, and a cycloheptenyl group. For example, these alkenyl groups may be substituted or not. For example, an alkenyl group may have 2 to 40 carbon atoms.

As used herein, the term "alkynyl group" refers to a hydrocarbon group including 2 to 20 carbon atoms with at least one carbon-carbon triple bond. Non-limiting examples of the alkynyl group are an ethynyl group, a 1-propynyl group, a 1-butynyl group, and a 2-butynyl group. For examples, these alkynyl groups may be substituted or not. For example, an alkynyl group may have 2 to 40 carbon atoms.

As used herein, the term "aromatic" refers to a ring or ring system with a conjugated π electron system, and may refer to a carbocyclic aromatic group (for example, a phenyl group and a heterocyclic aromatic group (for example, a pyridine group). For example, an aromatic ring system as a whole may include a single ring or a fused polycyclic ring (i.e., a ring that shares adjacent atom pairs).

As used herein, the terms "aryl group" refers to an aromatic ring or ring system (i.e., a ring fused from at least two rings, which shares two or more adjacent carbon atoms) of at least two ring including only carbon atoms in its backbone. When the aryl group is a ring system, each ring in the ring system may be aromatic. Non-limiting examples of the aryl group are a phenyl group, a biphenyl group, a naphthyl group, a phenanthrenyl group, and a naphthacenyl group. These aryl groups may be substituted or not.

As used herein, the term "heteroaryl group" refers to an aromatic ring system with one or plural fused rings, in which at least one member of a ring is a heteroatom, i.e., not carbon. In the fused ring system, at least one heteroatom may be in one ring. For example, the heteroatom may be oxygen, sulfur, or nitrogen, etc. Non-limiting examples of the heteroaryl group are a furanyl group, a thienyl group, an imidazolyl group, a quinazolinyl group, a quinolinyl group, an isoquinolinyl group, a quinoxalinyl group, a pyridinyl group, a pyrrolyl group, an oxazolyl group, and an indolyl group.

As used herein, the terms "aralkyl group" or "alkylaryl group" refers to an aryl group linked to a substituent via an alkylene group, like a C7-C14 aralkyl group. Non-limiting examples of the aralkyl group or alkylaryl group are a benzyl group, a 2-phenylethyl group, a 3-phenylpropyl group, and a naphthylalkyl group. For example, the alkylene group may be a lower alkylene group (i.e., a C1-C4 alkylene group).

As used herein, the terms "cycloalkenyl group" refers to a non-aromatic carbocyclic ring or ring system with at least one double bond. For example, the cycloalkenyl group may be a cyclohexcenyl group.

As used herein, the terms "heterocyclic group" refers to a non-aromatic ring or ring system including at least one heteroatom in its cyclic backbone.

As used herein, the term "halogen" refers to a stable atom belonging to Group 17 of the periodic tables of elements, for example, fluorine, chlorine, bromine, or iodine. For example, the halogen atom may be fluorine and/or chlorine.

As used herein, a substituent may be derived by substitution of at least one hydrogen atom in an unsubstituted mother group with another atom or a functional group. Unless stated otherwise, a substituted functional group refers to a functional group substituted with at least one substituent selected from a C1-C40 alkyl group, a C2-C40 alkenyl group, a C3-C40 cycloalkyl group, a C3-C40 cycloalkenyl group, a C1-C40 alkyl group, and a C7-C40 aryl group. When a functional group is "optionally" substituted, it means that the functional group may be substituted with such a substituent as listed above.

As an additive, an amount of the sulfonate ester-based compound represented by Formula 1 in the organic electrolyte solution may be in a range of, for example, about 0.01 wt % to about 10 wt % based on the total weight of the organic electrolyte solution. The amount of the sulfonate ester-based compound may be appropriately adjusted. For example, an amount of the sulfonate ester-based compound in the organic electrolyte solution may be in a range of about 0.1 wt % to about 10 wt % based on the total weight of the organic electrolyte solution. For example, an amount of the sulfonate ester-based compound in the organic electrolyte solution may be in a range of about 0.1 wt % to about 7 wt % based on the total weight of the organic electrolyte solution. For example, an amount of the sulfonate ester-based compound in the organic electrolyte solution may be in a range of about 0.1 wt % to about 5 wt % based on the total weight of the organic electrolyte solution. For example, an amount of the sulfonate ester-based compound in the organic electrolyte solution may be in a range of about 0.1 wt % to about 3 wt % based on the total weight of the organic electrolyte solution. For example, an amount of the sulfonate ester-based compound in the organic electrolyte solution may be in a range of about 0.1 wt % to about 2 wt % based on the total weight of the organic electrolyte solution. For example, an amount of the sulfonate ester-based compound in the organic electrolyte solution may be in a range of about 0.2 wt % to about 1.5 wt % based on the total weight of the organic electrolyte solution. When the amount of the sulfonate ester-based compound of Formula 1 is within these ranges, a lithium battery including the organic electrolytic solution may have improved battery characteristics.

In the organic electrolyte solution, the first lithium salt may include at least one selected from $LiPF_6$, $LiBF_4$, $LiSbF_6$, $LiAsF_6$, $LiClO_4$, $LiCF_3SO_3$, $Li(CF_3SO_2)_2N$, $LiC_4F_9SO_3$, $LiAlO_2$, $LiAlCl_4$, $LiN(C_xF_{2x+1}SO_2)(C_yF_{2y+1}SO_2)$ (where 2≤x≤20 and 2≤y≤20), LiCl, and LiI, but embodiments are not limited thereto, and any material available as a lithium salt of an organic electrolyte solution in the art may be used.

A concentration of the first lithium salt in the organic electrolyte solution may be, for example, in a range of about 0.01 M to about 2.0 M, and the concentration of the first lithium salt in the organic electrolyte solution may be adjusted appropriately. When the concentration of the first lithium salt in the organic electrolyte solution is within this range, a lithium battery including the organic electrolytic solution may have improved battery characteristics.

The organic solvent used in the organic electrolytic solution may be a low-boiling point solvent. The low-boiling point solvent refers to a solvent having a boiling point of about 200° C. or lower at about 25° C. at 1 atmosphere.

For example, the organic solvent may include at least one selected from a dialkylcarbonate, a cyclic carbonate, a linear or cyclic ester, a linear or cyclic amide, an alicyclic nitrile, a linear or cyclic ether, and a derivative thereof.

In some embodiments, the organic solvent may include at least one selected from dimethylcarbonate (DMC), ethylmethylcarbonate (EMC), methylpropylcarbonate, ethylpropylcarbonate, diethylcarbonate (DEC), dipropylcarbonate, propylenecarbonate (PC), ethylenecarbonate (EC), butylenecarbonate, ethylpropionate, ethylbutyrate, acetonitrile, succinonitrile (SN), dimethylsulfoxide, dimethylformamide, dimethylacetamide, γ-valerolactone, γ-butyrolactone, and tetrahydrofuran, etc.

The organic electrolyte solution may further include another additive in addition to the sulfonate ester-based compound. When the organic electrolyte solution further includes another additive, performance of a lithium battery including the organic electrolyte solution may improve.

The additive further included in the organic electrolyte solution may be a cyclic carbonate compound or a second lithium salt.

For example, the organic electrolyte solution may further include a cyclic carbonate compound as an additive. The cyclic carbonate compound used as an additive may be selected from vinylene carbonate (VC), vinylene carbonate substituted with at least one substituent selected from a halogen, a cyano group (CN), and a nitro group ($NO_2$), vinylethylene carbonate (VEC), vinylethylene carbonate substituted with at least one substituent selected from a halogen, a cyano group (CN), and a nitro group ($NO_2$), fluoroethylene carbonate (FEC), and fluoroethylene carbonate substituted with at least one substituent selected from a halogen, a cyano group (CN), and a nitro group ($NO_2$). When the organic electrolyte solution further includes the cyclic carbonate compound as another additive, charging/discharging characteristics of a lithium battery using the organic electrolyte solution may further improve.

In the organic electrolyte solution, an amount of the cyclic carbonate compound may be in a range of, for example, about 0.01 wt % to about 5 wt % based on the total weight of the organic electrolyte solution, and the amount of the cyclic carbonate compound in the organic electrolyte solution may be adjusted appropriately. For example, in the organic electrolyte solution, an amount of the cyclic carbonate compound may be in a range of about 0.1 wt % to about 5 wt % based on the total weight of the organic electrolyte solution. For example, in the organic electrolyte solution, an amount of the cyclic carbonate compound may be in a range of about 0.1 wt % to about 4 wt % based on the total weight of the organic electrolyte solution. For example, in the organic electrolyte solution, an amount of the cyclic carbonate compound may be in a range of about 0.1 wt % to about 3 wt % based on the total weight of the organic electrolyte solution. For example, in the organic electrolyte solution, an amount of the cyclic carbonate compound may be in a range of about 0.1 wt % to about 2 wt % based on the total weight of the organic electrolyte solution. For example, in the organic electrolyte solution, an amount of the cyclic carbonate compound may be in a range of about 0.2 wt % to about 2 wt % based on the total weight of the organic electrolyte solution. For example, in the organic electrolyte solution, an amount of the cyclic carbonate compound may be in a range of about 0.2 wt % to about 1.5 wt % based on the total weight of the organic electrolyte solution. When the amount of the cyclic carbonate compound in the organic electrolyte solution is within these ranges, a lithium battery including the organic electrolyte solution may have improved battery characteristics.

For example, the organic electrolyte solution may further include a second lithium salt as an additive. The second lithium salt is a lithium salt that is different from the first lithium salt, and examples of the second lithium salt may include oxalate, $PO_2F_2^-$, and $N(SO_2F)_2^-$. For example, the second lithium salt may be a compound represented by one of Formulae 23 to 30:

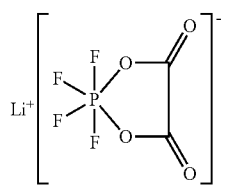

<Formula 23>

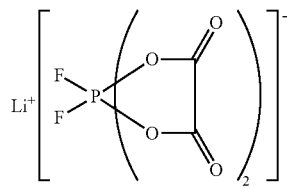

<Formula 24>

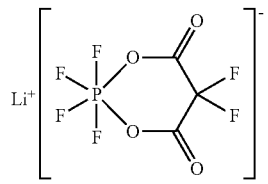

<Formula 25>

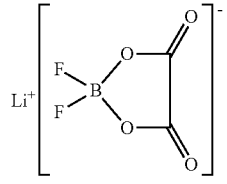

<Formula 26>

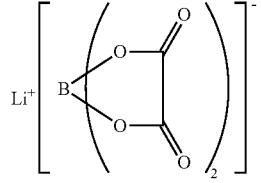

<Formula 27>

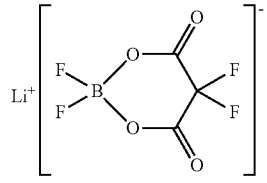

<Formula 28>

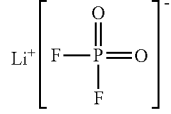

<Formula 29>

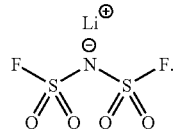

<Formula 30>

In the organic electrolyte solution, an amount of the second lithium salt may be in a range of, for example, about 0.1 wt % to about 5 wt % based on the total weight of the organic electrolyte solution, and the amount of the second lithium salt may be adjusted appropriately. For example, an amount of the second lithium salt may be in a range of about 0.1 wt % to about 5 wt % based on the total weight of the organic electrolyte solution. For example, an amount of the second lithium salt may be in a range of about 0.1 wt % to about 4 wt % based on the total weight of the organic electrolyte solution. For example, an amount of the second lithium salt may be in a range of about 0.1 wt % to about 3 wt % based on the total weight of the organic electrolyte solution. For example, an amount of the second lithium salt may be in a range of about 0.1 wt % to about 2 wt % based on the total weight of the organic electrolyte solution. For example, an amount of the second lithium salt may be in a range of about 0.2 wt % to about 2 wt % based on the total weight of the organic electrolyte solution. For example, an amount of the second lithium salt may be in a range of about 0.2 wt % to about 1.5 wt % based on the total weight of the organic electrolyte solution. When the amount of the second lithium salt in the organic electrolyte solution is within these ranges, a lithium battery including the organic electrolyte solution may have improved battery characteristics.

The organic electrolytic solution may be in a liquid or gel phase. The organic electrolytic solution may be prepared by adding a first lithium salt and the additive described above into the organic solvent described above.

According to another embodiment, a lithium battery includes a cathode, an anode, and any of the organic electrolytic solutions according to the above-described embodiments. The lithium battery may be, for example, a lithium primary battery, or a lithium secondary battery such as a lithium ion battery, a lithium ion polymer battery, a lithium sulfur battery, etc.

For example, the anode of the lithium battery may include graphite. For example, the cathode in the lithium battery may include a lithium transition metal oxide having a nickel-containing layered structure. For example, the lithium battery may have a high voltage of about 3.80 V or higher. For example, the lithium battery may have a high voltage of about 4.0 V or higher. For example, the lithium battery may have a high voltage of about 4.35 V or higher.

For example, the lithium battery may be prepared using a method described below.

First, a cathode is prepared.

For example, a cathode active material, a conducting agent, a binder, and a solvent may be mixed to prepare a cathode active material composition. The cathode active material composition may be directly coated on a metallic current collector to prepare a cathode plate. In another implementation, the cathode active material composition may be cast on a separate support to form a cathode active material film, which may then be separated from the support and laminated on a metallic current collector to prepare a cathode plate. The cathode may be one of a variety of types.

The cathode active material may be, for example, a lithium-containing metal oxide, etc. For example, the cathode active material may be at least one composite oxide of lithium and a metal selected from cobalt, manganese, nickel, and a combination thereof. For example, the cathode active material may be a compound represented by one of the following formulae: $Li_aA_{1-b}B_bD_2$ (where $0.90 \leq a \leq 1.8$, and $0 \leq b \leq 0.5$), $Li_aE_{1-b}B_bO_{2-c}D_c$ (where $0.90 \leq a \leq 1.8$, $0 \leq b \leq 0.5$, $0 \leq c \leq 0.05$), $LiE_{2-b}B_bO_{4-c}D$ (where $0 \leq b \leq 0.5$, $0 \leq c \leq 0.05$), $Li_aNi_{1-b-c}Co_bB_cD_\alpha$ (where $0.90 \leq a \leq 1.8$, $0 \leq b \leq 0.5$, $0 \leq c \leq 0.05$, $0 < \alpha \leq 2$), $Li_aNi_{1-b-c}Co_bB_cO_{2-\alpha}F_\alpha$ (where $0.90 \leq a \leq 1.8$, $0 \leq b \leq 0.5$, $0 \leq c \leq 0.05$, $0 < \alpha < 2$), $Li_aNi_{1-b-c}Co_bB_cO_{2-\alpha}F_2$ (where $0.90 \leq a \leq 1.8$, $0 \leq b \leq 0.5$, $0 \leq c \leq 0.05$, $0 < \alpha < 2$), $Li_aNi_{1-b-c}Mn_bB_cD_\alpha$ (where $0.90 \leq a \leq 1.8$, $0 \leq b \leq 0.5$, $0 \leq c \leq 0.05$, $0 < \alpha \leq 2$), $Li_aNi_{1-b-c}Mn_bB_cO_{2-\alpha}F_\alpha$ (where $0.90 \leq a \leq 1.8$, $0 \leq b \leq 0.5$, $0 \leq c \leq 0.05$, $0 < \alpha < 2$), $Li_aNi_{1-b-c}Mn_bB_cO_{2-\alpha}F_2$ (where $0.90 \leq a \leq 1.8$, $0 \leq b \leq 0.5$, $0 \leq c \leq 0.05$, $0 < \alpha < 2$), $Li_aNi_bE_cG_dO_2$ (where $0.90 \leq a \leq 1.8$, $0 \leq b \leq 0.9$, $0 \leq c \leq 0.5$, $0.001 \leq d \leq 0.1$), $Li_aNi_bCo_cMn_dGeO_2$ (where $0.90 \leq a \leq 1.8$, $0 \leq b \leq 0.9$, $0 \leq c \leq 0.5$, $0 \leq d \leq 0.5$, $0.001 \leq e \leq 0.1$), $Li_aNiG_bO_2$ (where $0.90 \leq a \leq 1.8$, $0.001 \leq b \leq 0.1$), $Li_aCoG_bO_2$ (where $0.90 \leq a \leq 1.8$, $0.001 \leq b \leq 0.1$), $Li_aMnG_bO_2$ (where $0.90 \leq a \leq 1.8$, $0.001 \leq b \leq 0.1$), $Li_aMn_2GbO_4$ (where $0.90 \leq a \leq 1.8$, $0.001 \leq b \leq 0.1$), $QO_2$, $QS_2$, $LiQS_2$, $V_2O_5$, $LiV_2O_5$, $LiIO_2$, $LiNiVO_4$, $Li_{(3-f)}J_2(PO_4)_3$ ($0 \leq f \leq 2$), $Li_{(3-f)}Fe_2(PO_4)_3$ ($0 \leq f \leq 2$), and $LiFePO_4$:

In the formulae above, A may be selected from the group of nickel (Ni), cobalt (Co), manganese (Mn), and combinations thereof, B may be selected from the group of aluminum (Al), nickel (Ni), cobalt (Co), manganese (Mn), chromium (Cr), iron (Fe), magnesium (Mg), strontium (Sr), vanadium (V), a rare earth element, and combinations thereof, D may be selected from the group of oxygen (O), fluorine (F), sulfur (S), phosphorus (P), and combinations thereof, E may be selected from the group of cobalt (Co), manganese (Mn), and combinations thereof, F may be selected from the group of fluorine (F), sulfur (S), phosphorus (P), and combinations thereof, G is selected from the group of aluminum (Al), chromium (Cr), manganese (Mn), iron (Fe), magnesium (Mg), lanthanum (La), cerium (Ce), strontium (Sr), vanadium (V), and combinations thereof, Q may be selected from the group of titanium (Ti), molybdenum (Mo), manganese (Mn), and combinations thereof, I may be selected from the group of chromium (Cr), vanadium (V), iron (Fe), scandium (Sc), yttrium (Y), and combinations thereof, and J may be selected from the group of vanadium (V), chromium (Cr), manganese (Mn), cobalt (Co), nickel (Ni), copper (Cu), and combinations thereof.

In some embodiments, the cathode active material may be $LiCoO_2$, $LiMn_xO_{2x}$ (x=1, 2), $LiNi_{1-x}Mn_xO_{2x}$ ($0<x<1$), $LiNi_{1-x-y}Co_xMn_yO_2$ ($0 \leq x \leq 0.5$, $0 \leq y \leq 0.5$), or $LiFePO_4$.

A lithium-containing metal oxide having a coating layer on surfaces thereof may be used as a cathode active material. In another implementation, a mixture of a lithium-containing metal oxide without a coating layer and a lithium-containing metal oxide having a coating layer may be used. The coating layer may include at least one compound of a coating element selected from the group of oxide, hydroxide, oxyhydroxide, oxycarbonate, and hydroxycarbonate of the coating element. The compounds for the coating layer may be amorphous or crystalline. The coating element for the coating layer may be magnesium (Mg), aluminum (Al), cobalt (Co), potassium (K), sodium (Na), calcium (Ca), silicon (Si), titanium (Ti), vanadium (V), tin (Sn), germanium (Ge), gallium (Ga), boron (B), arsenic (As), zirconium (Zr), or mixtures thereof. The coating layer may be formed using a suitable method that does not adversely affect the physical properties of the cathode active material when a compound of the coating element is used. For example, the coating layer may be formed using a spray coating method, a dipping method, or the like.

The conducting agent may be, for example, carbon black or graphite particulates, or another suitable conducting agent.

Examples of the binder are a vinylidene fluoride/hexafluoropropylene copolymer, polyvinylidene fluoride (PVDF), polyacrylonitrile, polymethylmethacrylate, polytetrafluoroethylene, mixtures thereof, a styrene butadiene rubber polymer, or another suitable material available as a binding agent.

Examples of the solvent are N-methyl-pyrrolidone, acetone, water, or another suitable material available as a solvent.

The amounts of the cathode active material, the conducting agent, the binder, and the solvent may be in suitable ranges. The conducting agent, the binder, or the solvent may not be used according to the use and the structure of the lithium battery.

Next, an anode may be prepared.

For example, an anode active material, a conducting agent, a binder, and a solvent may be mixed to prepare an anode active material composition. The anode active material composition is directly coated on a metallic current collector and dried to prepare an anode plate. In another implementation, the anode active material composition may be cast on a separate support to form an anode active material film, which may then be separated from the support and laminated on a metallic current collector to prepare an anode plate.

The anode active material may be a suitable anode active material for a lithium battery. For example, the anode active material may include at least one selected from the group of lithium metal, a metal that is alloyable with lithium, a transition metal oxide, a non-transition metal oxide, and a carbonaceous material.

Examples of the metal alloyable with lithium are Si, Sn, Al, Ge, Pb, Bi, Sb, a Si—Y alloy (where Y is an alkali metal, an alkali earth metal, a Group XIII element, a Group XIV element, a transition metal, a rare earth element, or a combination thereof except for Si), and a Sn—Y alloy (where Y is an alkali metal, an alkali earth metal, a Group XIII element, a Group XIV element, a transition metal, a rare earth element, or a combination thereof except for Sn). Y may be magnesium (Mg), calcium (Ca), strontium (Sr), barium (Ba), radium (Ra), scandium (Sc), yttrium (Y), titanium (Ti), zirconium (Zr), hafnium (Hf), rutherfordium (Rf), vanadium (V), niobium (Nb), tantalum (Ta), dubnium (Db), chromium (Cr), molybdenum (Mo), tungsten (W), seaborgium (Sg), technetium (Tc), rhenium (Re), bohrium (Bh), iron (Fe), lead (Pb), ruthenium (Ru), osmium (Os), hassium (Hs), rhodium (Rh), iridium (Ir), palladium (Pd), platinum (Pt), copper (Cu), silver (Ag), gold (Au), zinc (Zn), cadmium (Cd), boron (B), aluminum (Al), gallium (Ga), tin (Sn), indium (In), titanium (Ti), germanium (Ge), phosphorus (P), arsenic (As), antimony (Sb), bismuth (Bi), sulfur (S), selenium (Se), tellurium (Te), polonium (Po), or combinations thereof.

Examples of the transition metal oxide are a lithium titanium oxide, a vanadium oxide, a lithium vanadium oxide, etc.

For example, the non-transition metal oxide may be $SnO_2$, or $SiO_x$ ($0<x<2$).

Examples of the carbonaceous material are crystalline carbon, amorphous carbon, and mixtures thereof. Examples of the crystalline carbon are graphite, such as natural graphite or artificial graphite that are in amorphous, plate, flake, spherical or fibrous form. Examples of the amorphous carbon are soft carbon (carbon sintered at low temperatures), hard carbon, meso-phase pitch carbides, sintered corks, and the like.

The conducting agent, the binder, and the solvent used for the anode active material composition may be the same as those used for the cathode active material composition.

Suitable amounts of the anode electrode active material, the conducting agent, the binder, and the solvent may be used. The conducting agent, the binder, or the solvent may not be used according to the use and the structure of the lithium battery.

Next, a separator may be prepared, to be disposed between the cathode and the anode.

The separator may be a suitable separator for use in lithium batteries. The separator may have low resistance to migration of ions in an electrolyte and have an excellent electrolyte-retaining ability. Examples of the separator are glass fiber, polyester, Teflon, polyethylene, polypropylene, polytetrafluoroethylene (PTFE), and a combination thereof, each of which may be a non-woven or woven fabric. For example, a rollable separator including polyethylene or polypropylene may be used for a lithium ion battery. A separator with a good organic electrolytic solution-retaining ability may be used for a lithium ion polymer battery. For example, the separator may be manufactured in the following manner.

A polymer resin, a filler, and a solvent may be mixed together to prepare a separator composition. Then, the separator composition may be directly coated on an electrode, and then dried to form the separator. In another implementation, the separator composition may be cast on a support and then dried to form a separator film, which may then be separated from the support and laminated on an electrode to form the separator.

The polymer resin used to manufacture the separator may be a suitable material for use as a binder for electrode plates. Examples of the polymer resin are a vinylidenefluoride/hexafluoropropylene copolymer, polyvinylidene fluoride (PVDF), polyacrylonitrile, polymethylmethacrylate, and a mixture thereof.

Next, an organic electrolytic solution as described in the previous embodiments may be prepared.

Figure 2:
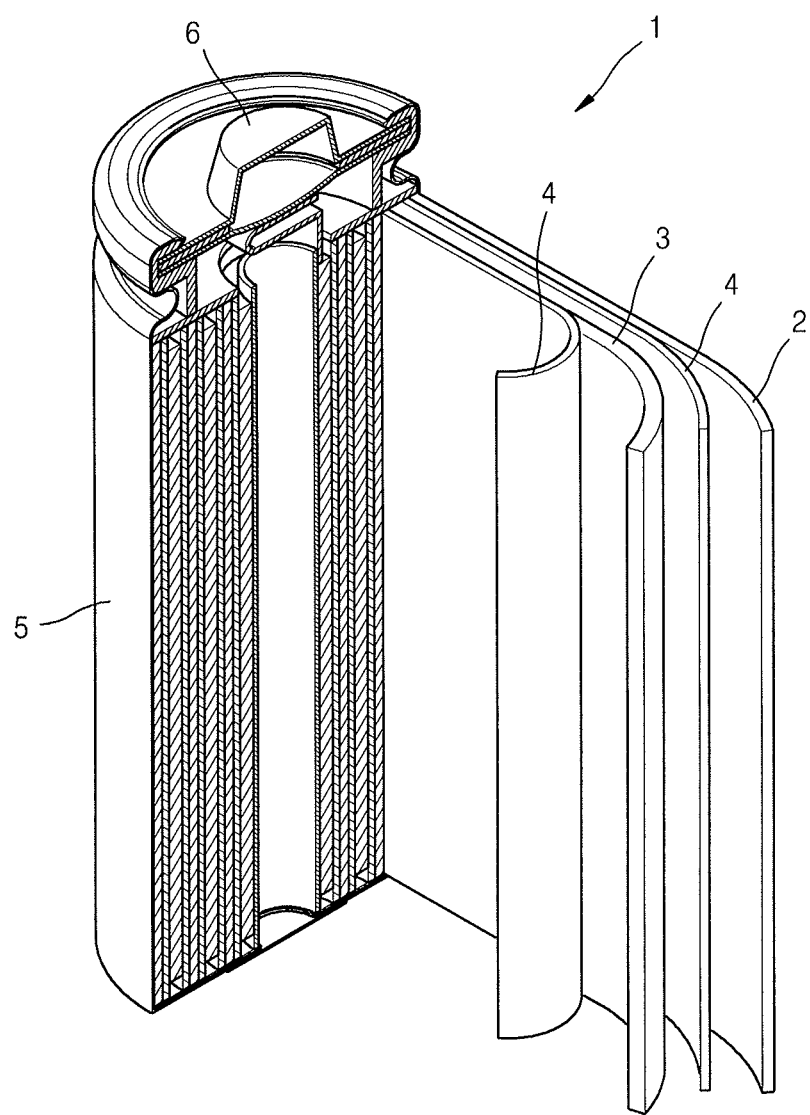
FIG. 2 illustrates a schematic view of a lithium battery according to an embodiment of the present disclosure.

Referring to FIG. 2, a lithium battery 1 includes a cathode 3, an anode 2, and a separator 4. The cathode 3, the anode 2, and the separator 4 may be stacked, wound, or folded, and then sealed in a battery case 5. Then, the battery case 5 may be filled with an organic electrolytic solution and sealed with a cap assembly 6, thereby completing the manufacture of the lithium battery 1. The battery case 5 may be, for example, a cylindrical type, a rectangular type, a thin-film type, etc.

The separator may be interposed between the cathode and the anode to form a battery assembly. In another implementation, the battery assembly may be stacked in a bi-cell structure and impregnated with the electrolytic solution. The resultant may be put into a pouch and hermetically sealed, thereby completing the manufacture of a lithium battery.

In another implementation, a plurality of battery assemblies may be stacked to form a battery pack, which may be used in a device that operates at high temperatures and requires high output, for example, in a laptop computer, a smart phone, or an electric vehicle.

The lithium battery may have improved lifetime characteristics and high rate characteristics, and thus may be applicable in an electric vehicle (EV), for example, in a hybrid vehicle such as plug-in hybrid electric vehicle (PHEV). The lithium battery may be applicable to the high-power storage field, or, for example, in an electric bicycle or a power tool.

The following Examples and Comparative Examples are provided in order to highlight characteristics of one or more embodiments, but it will be understood that the Examples and Comparative Examples are not to be construed as limiting the scope of the embodiments, nor are the Comparative Examples to be construed as being outside the scope of the embodiments. Further, it will be understood that the embodiments are not limited to the particular details described in the Examples and Comparative Examples.

(Synthesis of Additives)

Preparation Example 1: Synthesis of Compound of Formula 7

A compound represented by Formula 7 below was prepared according to Reaction Scheme 1 below:

<Reaction Scheme 1>

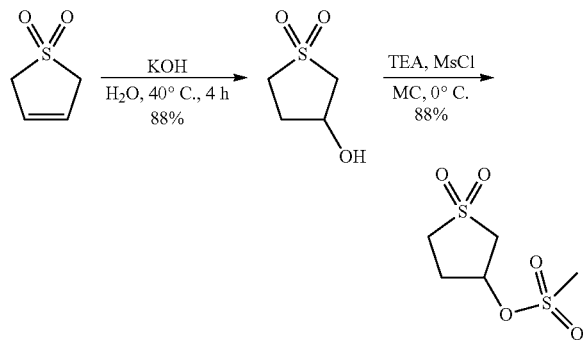

(Synthesis of Compound A)

<Step 1>

5.0 g (42.2 mmol) of 2,5-dihydrothiophene-1,1-dioxide and 2.6 g (46.6 mmol) of potassium hydroxide were dissolved in 7 ml of water to prepare a mixture. The mixture was reflux-heated at 40° C. for 4 hours to allow a reaction to occur in the mixture. The reaction product was cooled to room temperature, and a concentrated hydrochloric acid aqueous solution (at a concentration of 35 to 37%) was used to neutralize the reaction product to a pH of 6 to 7. 500 ml of cold acetone was added to the neutralized reaction product, filtered by using a reduced-pressure filtering device to remove precipitated potassium chloride. Acetone was removed from the filtered solution at a reduced pressure to obtain a white solid. The white solid was dissolved in the minimum amount of acetone and passed through a silica gel using ethyl acetate as an eluent to remove the remaining potassium chloride. The filtered solution was concentrated to obtain a yellow liquid.

(88%) $^1$H NMR (400 MHz, CDCl$_3$) 4.74 (s, 1H), 3.40-3.25 (m, 2H), 3.18-3.12 (m, 2H), 2.38 (br, 2H)

<Step 2>

3.3 g (24.15 mmol) of 3-hydroxytetrahydrothiophene-1,1-dioxide synthesized in Step 1 was dissolved in 15 ml of dichloromethane (MC, methylene chloride) and cooled to 0° C. 3.36 ml (24.6 mmol) of triethanolamine (TEA) was added to the cooled solution, and 1.87 ml (24.15 mmol) of methanesulfonyl chloride (MsCl) was slowly and dropwisely added thereto. The mixture thus obtained was allowed to react at 0° C. for 50 minutes, and the precipitate in the mixture was removed by passing the mixture through a silica gel. Here, an eluent used in the silica gel was ethyl acetate. The filtered solution after passing through the silica gel was concentrated under a reduced pressure, and recrystallized by using dichloromethane to obtain a white solid at a yield of 88%.

$^1$H NMR (400 MHz, CDCl$_3$): 5.10 (m, 1H), 3.42 (d, J=11 Hz, 2H), 3.35-3.19 (m, 2H), 3.12 (s, 3H), 2.68-2.57 (m, 2H), $^{13}$C NMR (100 MHz, CDCl$_3$): 74.67, 56.96, 49.00, 39.13, 30.33,

<Formula 7>

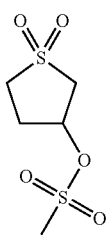

(Preparation of Organic Electrolyte Solution)

Example 1: SEI-1456 1.0 wt %

A solution of 1.50 M LiPF$_6$, as a lithium salt, and 1 wt % of a compound represented by Formula 7 was formed in a mixed solvent of ethylenecarbonate (EC), ethylmethylcarbonate (EMC), and diethylcarbonate (DEC) (volume ratio of 2:2:6) as an organic electrolytic solution.

<Formula 7>

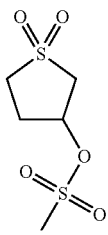

Example 2: SEI-1456 1.0 wt %+VC 0.5 wt %

An organic electrolytic solution was prepared in the same manner as in Example 1, except that the additive was changed to 1 wt % of the compound of Formula 7 and 0.5 wt % of vinylene carbonate (VC) of Formula 31.

<Formula 31>

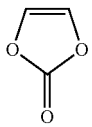

Example 3: SEI-1456 0.5 wt %

An organic electrolytic solution was prepared in the same manner as in Example 1, except that an amount of the compound of Formula 7 as an additive was changed to 0.5 wt %.

Comparative Example 1: CTL

An organic electrolytic solution was prepared in the same manner as in Example 1, except that the compound of Formula 7 as an additive was not added.

Comparative Example 2: CTL

An organic electrolytic solution was prepared in the same manner as in Example 1, except that a compound of Formula 32 was used instead of the compound of Formula 7 as an additive.

<Formula 32>

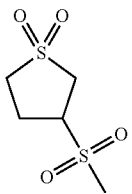

Preparation of Lithium Battery

Example 4

(Preparation of Anode)

About 98 wt % of artificial graphite (BSG-L, available from Tianjin BTR New Energy Technology Co., Ltd.), about 1.0 wt % of styrene-butadiene rubber (SBR) binder (available from ZEON), and about 1.0 wt % of carboxymethylcellulose (CMC, available from NIPPON A&L) were mixed with distilled water and stirred using a mechanical stirrer for about 60 minutes to prepare an anode active material slurry. The anode active material slurry was coated on a 10 μm-thick Cu current collector to a thickness of about 60 μm with a doctor blade. Then, the resultant was dried in a hot-air dryer at about 100° C. for about 0.5 hour, and then at about 120° C. in a vacuum for 4 hours, followed by roll-pressing to prepare an anode plate.

(Preparation of Cathode)

About 97.45 wt % of $LiNi_{1/3}Co_{1/3}Al_{1/3}O_2$, about 0.5 wt % of artificial graphite (SFG6, available from Timcal) powder as a conducting agent, about 0.7 wt % of carbon black (Ketjen black, available from ECP), about 0.25 wt % of modified acrylonitrile rubber (BM-720H, available from Zeon Corporation), about 0.9 wt % of polyvinylidenefluoride (PVdF, S6020, available from Solvay), and about 0.2 wt % of polyvinylidenefluoride (PVdF, S5130, available from Solvay) were mixed with N-methyl-2-pyrrolidone as a solvent and stirred for about 30 minutes to prepare a cathode active material slurry. The cathode active material slurry was coated on a 20 μm-thick aluminum (Al) current collector to a thickness of about 60 μm with a doctor blade. Then, the resultant was dried in a hot-air dryer at about 100° C. for about 0.5 hour, and then at about 120° C. in a vacuum for 4 hours, followed by roll-pressing to manufacture a cathode plate.

A 14 μm-thick polyethylene separator with a ceramic coating on a surface facing the cathode, and the organic electrolytic solution of Example 1 above were used to prepare a lithium battery.

Examples 5 and 6

Lithium batteries were manufactured in the same manner as in Example 4, except that the organic electrolytic solutions of Examples 2 and 3 instead of the organic electrolytic solution of Example 1 were used, respectively.

Comparative Examples 3 and 4

Lithium batteries were manufactured in the same manner as in Example 4, except that the organic electrolytic solutions of Comparative Examples 1 and 2 instead of the organic electrolytic solution of Example 1 were used, respectively.

Evaluation Example 1: Evaluation of 4.2 V Room-Temperature (25° C.) Charge-Discharge Characteristics The lithium batteries of Examples 4 to 6 and Comparative Examples 3 and 4 were each charged at a constant current of 0.1 C rate at about 25° C. to a voltage of about 4.2 V, and then charged at a constant voltage of about 4.2 V to a current of about 0.05 C (cut-off current), followed by discharging with a constant current of 0.1 C until the voltage reached about 2.5 V (formation process, 1st cycle).

Each of the lithium batteries through the $1^{st}$ cycle of the formation process was charged at a constant current of 0.2 C rate at about 25° C. to a voltage of about 4.2 V, and then charged at a constant voltage of about 4.2 V to a current of 0.05 C (cut-off current), followed by discharging with a constant current of 0.2 C until the voltage reached about 2.5 V (formation process, $2^{nd}$ cycle).

The lithium battery through the $3^{rd}$ cycle of the formation process was charged at a constant current of 1.0 C rate at about 25° C. to a voltage of about 4.2 V, and then charged at a constant voltage of about 4.2 V to a current of 0.05 C (cut-off current), followed by discharging with a constant current of about 1.0 C until the voltage reached about 2.5 V. This cycle of charging and discharging was repeated 400 times.

A rest time of about 10 minutes was allowed after each charge and discharge cycle.

Charge-discharge test results are shown in Table 1 and FIG. 1. A capacity retention at 400 cycles may be defined by Equation 1.

Capacity retention rate=[Discharge capacity at $400^{th}$ cycle/Discharge capacity at $1^{st}$ cycle]×100    <Equation 1>

TABLE 1

|  | Discharge capacity at $400^{th}$ cycle [mAh/g] | Discharge capacity at $400^{th}$ cycle [%] |
|---|---|---|
| Example 4 | 2325 | 89.2 |
| Example 5 | 2370 | 91.0 |
| Example 6 | 2309 | 88.1 |
| Comparative Example 3 | 2262 | 87.1 |
| Comparative Example 4 | 2283 | 87.4 |

Referring to Table 1 and FIG. 1, the lithium batteries of Examples 4 to 6 including the compound of Formula 3 according to an embodiment as an additive were found to have improved room-temperature discharge capacities and improved lifetime characteristics, compared to the lithium batteries of Comparative Examples 2 and 3 including no additive and an additive having a structure different from that of the present disclosure, respectively.

Evaluation Example 6: Direct Current-Internal Resistance (DC-IR) Evaluation after Preserving at High Temperature of 60° C.

The lithium batteries prepared in Examples 4 to 6 and Comparative Examples 3 and 4 were each charged at a constant current of 0.5 C rate at about 25° C. to a voltage of about 4.2 V (vs. Li), and then charged at a constant voltage of about 4.2 V to a current of about 0.05 C (cut-off current), and thus the battery was charged to a 100% state of charge (SOC) voltage.

Direct current-internal resistances (DC-IRs) of the charged lithium batteries and DC-IRs of the charged lithium batteries preserved in a 60° C. oven for 20 days were measured as follows. The DC-IRs of the charged lithium batteries before the 20 days preservation are referred to as initial DC-IRs, and the DC-IRs of the charged lithium batteries after the 20 days preservation are referred to as DC-IRs after preserving at high temperature.

The batteries were each discharged at a constant current of 0.5 C rate for 30 seconds, rested for 30 seconds, charged at a constant current of 0.5 C for 30 seconds, and rested for 10 minutes, discharged at a constant current of 1.0 C rate for 30 seconds, rested for 30 seconds, charged at a constant current of 0.5 C for 1 minute, and rested for 10 minutes, discharged at a constant current of 2.0 C rate for 30 seconds, rested for 30 seconds, charged at a constant current of 0.5 C for 2 minutes, and rested for 10 minutes, and discharged at a constant current of 3.0 C rate for 30 seconds, rested for 30 seconds, charged at a constant current of 0.5 C for 3 minutes, and rested for 10 minutes.

An average voltage drop value for 30 second for each C-rate is a direct current resistance value ($\Delta V/\Delta I = R$).

DC-IR increase rates calculated by using the initial DC-IRs and DC-IRs after preserving at high temperature thus measured are shown in Table 2. The DC-IR increase rates are defined by Equation 2.

DC-IR increase rate [%]=[DC-IR after preserving at high temperature/initial DC-IR]×100     <Equation 2>

TABLE 2

| | Initial DC-IR [mΩ] | DC-IR after 20 days of perseverance [mΩ] | DC-IR increase rate after 20 days of preservation [%] |
|---|---|---|---|
| Example 4 | 36.8 | 42.9 | 117 |
| Example 5 | 36.9 | 43.2 | 117 |
| Example 6 | 36.5 | 43.5 | 119 |
| Comparative Example 3 | 36.3 | 44.0 | 121 |
| Comparative Example 4 | 36.2 | 44.2 | 122 |

As shown in Table 2, the lithium batteries of Examples 4 to 6 including the organic electrolyte solution of the present disclosure had decreased DC-IR increase rates after being preserved at high temperature compared to those of the lithium batteries of Comparative Examples 3 and 4 not including the organic electrolyte solution of the present disclosure.

Therefore, high temperature perseverance stability of the lithium batteries improved, and thus output characteristics of the lithium batteries improved as well.

By way of summation and review, a lithium battery operating at a high driving voltage may be incompatible with an aqueous electrolytic solution highly reactive to lithium. For this reason, the lithium battery may use an organic electrolytic solution. The organic electrolytic solution may be prepared by dissolving a lithium salt in an organic solvent. An appropriate organic solvent may be stable at high voltages and may have a high ionic conductivity, a high dielectric constant, and a low viscosity.

Using an organic electrolyte solution including a carbonate-based polar, non-aqueous solvent in a lithium battery may cause a side reaction between an anode and/or a cathode and the organic electrolytic solution during initial charging, and consequentially lead to an irreversible reaction using excess charges.

Due to the irreversible reaction, a passivation layer such as a solid electrolyte interface (SEI) layer is formed on a surface of an anode. Also, a protection layer is formed on a surface of a cathode due to the irreversible reaction.

An SEI layer and/or a protection layer formed by using a general organic electrolyte solution may be easily degraded at a high temperature. Thus, the SEI layer and/or the protection layer may have poor stability at high temperatures.

As described above, according to the one or more of the above embodiments, high-temperature characteristics and lifespan characteristics of a lithium battery may improve by using an organic electrolytic solution including a sulfonate ester-based additive having a novel structure.

Example embodiments have been disclosed herein, and although specific terms are employed, they are used and are to be interpreted in a generic and descriptive sense only and not for purpose of limitation. In some instances, as would be apparent to one of ordinary skill in the art as of the filing of the present application, features, characteristics, and/or elements described in connection with a particular embodiment may be used singly or in combination with features, characteristics, and/or elements described in connection with other embodiments unless otherwise specifically indicated. Accordingly, it will be understood by those of skill in the art that various changes in form and details may be made without departing from the spirit and scope of the present invention as set forth in the following claims.

What is claimed is:
1. An organic electrolyte solution, comprising:
   a lithium salt;
   an organic solvent; and
   a sulfonate ester-based compound represented by Formula 1,

$R_2$—O—S(=O)$_2$—$R_1$     <Formula 1> wherein, in Formula 1,
   $R_1$ is a C1-C20 alkyl group that is unsubstituted or substituted with halogen, a C5-C20 cycloalkyl group that is unsubstituted or substituted with halogen, a C6-C40 aryl group that is unsubstituted or substituted with halogen, or a C2-C40 heteroaryl group that is unsubstituted or substituted with halogen, and
   $R_2$ is represented by Formula 2:

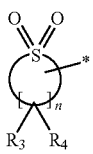

<Formula 2> wherein, in Formula 2,
$R_3$ and $R_4$ are each independently hydrogen, a C1-C20 alkyl group that is unsubstituted or substituted with halogen, a C2-C20 alkenyl group that is unsubstituted or substituted with halogen, a C2-C20 alkynyl group that is unsubstituted or substituted with halogen, a C5-C20 cycloalkyl group that is unsubstituted or substituted with halogen, a C6-C40 aryl group that is unsubstituted or substituted with halogen, a C2-C40 heteroaryl group that is unsubstituted or substituted with halogen, or a polar functional group having at least one heteroatom, n is an integer selected from 4 to 9, and

* represents the $R_2$-oxygen bond in Formula 2, provided that at least one of $R_3$ and $R_4$ is a C1-C20 alkyl group that is unsubstituted or substituted with halogen, a C2-C20 alkenyl group that is unsubstituted or substituted with halogen, a C2-C20 alkynyl group that is unsubstituted or substituted with halogen, a C5-C20 cycloalkyl group that is unsubstituted or substituted with halogen, a C6-C40 aryl group that is unsubstituted or substituted with halogen, a C2-C40 heteroaryl group that is unsubstituted or substituted with halogen, or a polar functional group having at least one heteroatom.

2. The organic electrolyte solution as claimed in claim 1, wherein:

at least one of $R_3$ and $R_4$ is the polar functional group having at least one heteroatom, and the polar functional group having at least one heteroatom includes at least one selected from —F, —Cl, —Br, —I, —C(=O)OR$^{16}$, —OC(=O)OR$^{16}$, —R$^{15}$OC(=O)OR$^{16}$, —C(=O)R$^{16}$, —R$^{15}$C(=O)R$^{16}$, —OC(=O)R$^{16}$, —R$^{15}$OC(=O)R$^{16}$, —C(=O)—O—C(=O)R$^{16}$, —R$^{15}$C(=O)—O—C(=O)R$^{16}$, —SR$^{16}$, —R$^{15}$SR$^{16}$, —SSR$^{16}$, —R$^{15}$SSR$^{16}$, —S(=O)R$^{16}$, —R$^{15}$S(=O)R$^{16}$, —R$^{15}$C(=S)R$^{16}$, —R$^{15}$C(=S)SR$^{16}$, —R$^{15}$SO$_3$R$^{16}$, —SO$_3$R$^{16}$, —NNC(=S)R$^{16}$, —R$^{15}$NNC(=S)R$^{16}$, —R$^{15}$N=C=S, —NCO, —R$^{15}$—NCO, —NO$_2$, —R$^{15}$NO$_2$, —R$^{15}$SO$_2$R$^6$, —SO$_2$R$^{16}$,

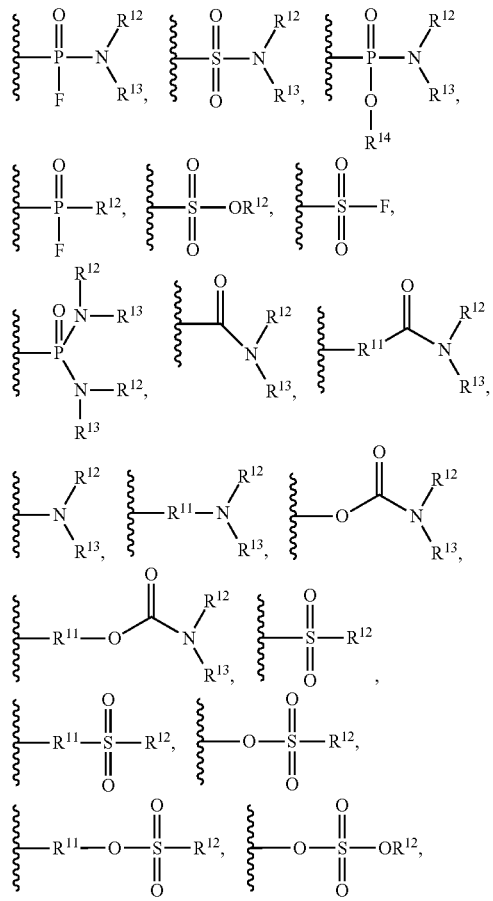

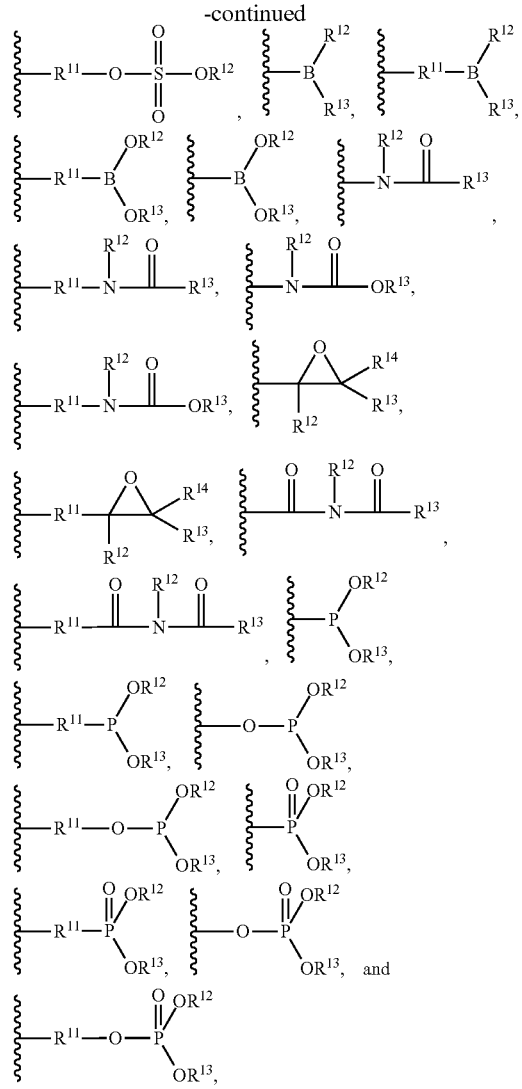

wherein $R^{11}$ and $R^{15}$ are each independently a C1-C20 alkylene group that is unsubstituted or substituted with halogen, a C2-C20 alkenylene group that is unsubstituted or substituted with halogen, a C2-C20 alkynylene group that is unsubstituted or substituted with halogen, a C3-C12 cycloalkylene group that is unsubstituted or substituted with halogen, a C6-C40 arylene group that is unsubstituted or substituted with halogen, a C2-C40 heteroarylene group that is unsubstituted or substituted with halogen, a C7-C15 alkylarylene group that is unsubstituted or substituted with halogen, or a C7-C15 aralkylene group that is unsubstituted or substituted with halogen, and $R^{12}$, $R^{13}$, $R^{14}$, and $R^{16}$ are each independently hydrogen, a halogen, a C1-C20 alkyl group that is unsubstituted or substituted with halogen, a C2-C20 alkenyl group that is unsubstituted or substituted with halogen, a C2-C20 alkynyl group that is unsubstituted or substituted with halogen, a C3-C12 cycloalkyl group that is unsubstituted or substituted with halogen, a C6-C40 aryl group that is unsubstituted or substituted with halogen, a C2-C40 heteroaryl group that is unsubstituted or substituted with halogen, a C7-C15 alkylaryl group that is unsubstituted or substituted with halogen, a C7-C15 trialkylsilyl group that is unsubstituted or substituted with halogen, or a C7-C15 aralkyl group that is unsubstituted or substituted with halogen.

3. The organic electrolyte solution as claimed in claim 1, wherein $R_2$ is a substituted or unsubstituted sulfolanyl group.

4. The organic electrolyte solution as claimed in claim 3, wherein:
the sulfolanyl group is substituted, and
the substituent of the sulfolanyl group is a C1-C20 alkyl group that is unsubstituted or substituted with halogen, a C2-C20 alkenyl group that is unsubstituted or substituted with halogen, a C2-C20 alkynyl group that is unsubstituted or substituted with halogen, a C5-C20 cycloalkyl group that is unsubstituted or substituted with halogen, a C6-C40 aryl group that is unsubstituted or substituted with halogen, a C2-C40 heteroaryl group that is unsubstituted or substituted with halogen, or a polar functional group having at least one heteroatom.

5. The organic electrolyte solution as claimed in claim 1, wherein the sulfonate ester-based compound of Formula 1 is represented by Formula 3 or Formula 4,

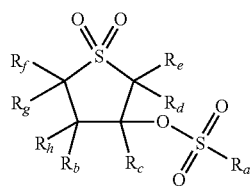

<Formula 3>

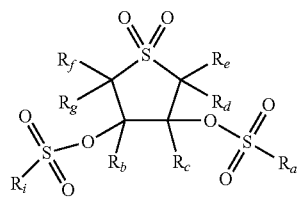

<Formula 4> wherein, in Formula 3 and Formula 4,
$R_a$ and $R_i$ are each independently a halogen, a C1-C20 alkyl group that is unsubstituted or substituted with halogen, a C5-C20 cycloalkyl group that is unsubstituted or substituted with halogen, a C6-C40 aryl group that is unsubstituted or substituted with halogen, or a C2-C40 heteroaryl group that is unsubstituted or substituted with halogen, and $R_b$, $R_c$, $R_d$, $R_e$, $R_f$, $R_g$, and $R_h$ are each independently hydrogen, a halogen, a C1-C20 alkyl group that is unsubstituted or substituted with halogen, a C2-C20 alkenyl group that is unsubstituted or substituted with halogen, a C2-C20 alkynyl group that is unsubstituted or substituted with halogen, a C1-C20 alkoxy group that is unsubstituted or substituted with halogen, a C5-C20 cycloalkyl group that is unsubstituted or substituted with halogen, a C6-C40 aryl group that is unsubstituted or substituted with halogen, or a C2-C40 heteroaryl group that is unsubstituted or substituted with halogen.

6. The organic electrolyte solution as claimed in claim 5, wherein $R_a$ and $R_i$ are each independently F, Cl, Br, I, a methyl group, an ethyl group, a propyl group, an isopropyl group, a butyl group, a tert-butyl group, a trifluoromethyl group, a tetrafluoroethyl group, a phenyl group, a naphthyl group, a tetrafluorophenyl group, a pyrrolyl group, or a pyridinyl group, and $R_b$, $R_c$, $R_d$, $R_e$, $R_f$, $R_g$, and $R_h$ are each independently hydrogen, F, Cl, Br, I, a methyl group, an ethyl group, a propyl group, an isopropyl group, a butyl group, a tert-butyl group, a trifluoromethyl group, a tetrafluoroethyl group, a phenyl group, a naphthyl group, a tetrafluorophenyl group, a pyrrolyl group, or a pyridinyl group.

7. The organic electrolyte solution as claimed in claim 1, wherein the sulfonate ester-based compound of Formula 1 is represented by Formula 5 or Formula 6,

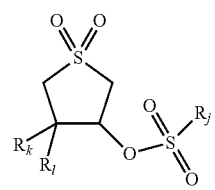

<Formula 5>

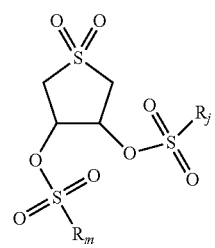

<Formula 6> wherein, in Formula 5 and Formula 6,
$R_j$ and $R_m$ are each independently a halogen, a C1-C20 alkyl group that is unsubstituted or substituted with halogen, a C6-C40 aryl group that is unsubstituted or substituted with halogen, or a C2-C40 heteroaryl group that is unsubstituted or substituted with halogen, and $R_k$ and $R_l$ are each independently hydrogen, a halogen, a C1-C20 alkyl group that is unsubstituted or substituted with halogen, a C6-C40 aryl group that is unsubstituted or substituted with halogen, or a C2-C40 heteroaryl group that is unsubstituted or substituted with halogen.

8. The organic electrolyte solution as claimed in claim 7, wherein $R_j$ and $R_m$ are each independently F, Cl, Br, I, a methyl group, an ethyl group, a propyl group, an isopropyl group, a butyl group, a tert-butyl group, a trifluoromethyl group, a tetrafluoroethyl group, a phenyl group, a naphthyl group, a tetrafluorophenyl group, a pyrrolyl group, or a pyridinyl group, and $R_k$ and $R_l$ are each independently hydrogen, F, Cl, Br, I, a methyl group, an ethyl group, a propyl group, an isopropyl group, a butyl group, a tert-butyl group, a trifluoromethyl group, a tetrafluoroethyl group, a phenyl group, a naphthyl group, a tetrafluorophenyl group, a pyrrolyl group, or a pyridinyl group.

9. The organic electrolyte solution as claimed in claim 1, wherein an amount of the sulfonate ester-based compound is in a range of about 0.01 wt % to about 10 wt % based on the total weight of the organic electrolyte solution.

10. The organic electrolyte solution as claimed in claim 1, wherein the lithium salt in the organic electrolyte solution includes at least one selected from $LiPF_6$, $LiBF_4$, $LiSbF_6$, $LiAsF_6$, $LiClO_4$, $LiCF_3SO_3$, $Li(CF_3SO_2)_2N$, $LiC_4F_9SO_3$, $LiAlO_2$, $LiAlCl_4$, $LiN(C_xF_{2x+1}SO_2)(C_yF_{2y+1}SO_2)$ (where $2 \leq x \leq 20$ and $2 \leq y \leq 20$), LiCl, and LiI.

11. An organic electrolyte solution, comprising:
a lithium salt;
an organic solvent; and
a sulfonate ester-based compound represented by one of the following Formulae 8 to 14, 16 18 to 22:
<Formula 8>
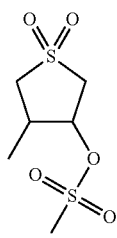
<Formula 9>
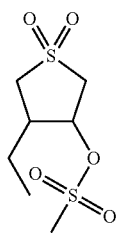
<Formula 10>
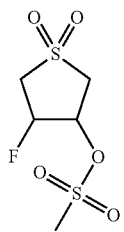
<Formula 11>
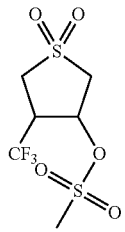
<Formula 12>
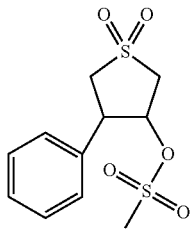
<Formula 13>
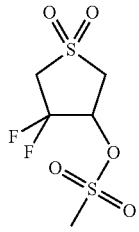
-continued
<Formula 14>
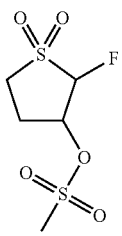
<Formula 16>
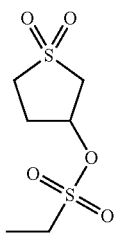
<Formula 18>
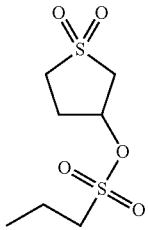
<Formula 19>
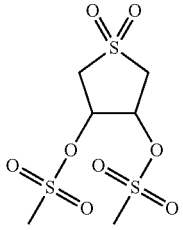
<Formula 20>
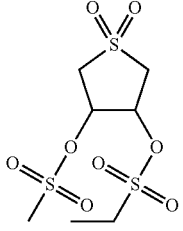
<Formula 21>
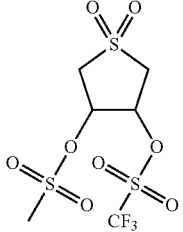

<Formula 22>

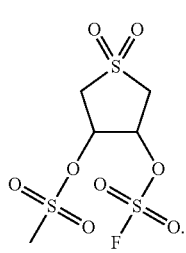

12. A lithium battery, comprising:
a cathode,
an anode, and
the organic electrolyte solution as claimed in claim 1.

13. The lithium battery as claimed in claim 12, wherein the cathode includes a lithium transition metal oxide having a nickel-containing layered structure.

14. The lithium battery as claimed in claim 12, wherein the lithium battery has a voltage of about 3.8 V or higher.

15. A lithium battery, comprising:
a cathode,
an anode, and
the organic electrolyte solution as claimed in claim 11.

* * * * *